(12) United States Patent
Nagakubo et al.

(10) Patent No.: US 9,721,752 B2
(45) Date of Patent: Aug. 1, 2017

(54) SAMPLE HOLDER AND CHARGED PARTICLE DEVICE

(71) Applicant: Hitachi High-Technologies Corporation, Minato-ku, Tokyo (JP)

(72) Inventors: Yasuhira Nagakubo, Tokyo (JP); Isao Nagaoki, Tokyo (JP); Hiroaki Matsumoto, Tokyo (JP); Takeshi Sato, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/912,553

(22) PCT Filed: May 19, 2014

(86) PCT No.: PCT/JP2014/063148
§ 371 (c)(1),
(2) Date: Feb. 17, 2016

(87) PCT Pub. No.: WO2015/045477
PCT Pub. Date: Apr. 2, 2015

(65) Prior Publication Data
US 2016/0211109 A1    Jul. 21, 2016

(30) Foreign Application Priority Data

Sep. 30, 2013   (JP) ................................. 2013-202952

(51) Int. Cl.
*H01J 37/00* (2006.01)
*H01J 37/20* (2006.01)
(Continued)

(52) U.S. Cl.
CPC .............. *H01J 37/20* (2013.01); *G01N 23/22* (2013.01); *H01J 37/18* (2013.01); *H01J 37/285* (2013.01);
(Continued)

(58) Field of Classification Search
CPC .......... H01J 37/20; H01J 37/285; H01J 37/18; H01J 2237/006; H01J 2237/2003; H01J 2237/2802; H01J 2237/188
(Continued)

(56) References Cited

U.S. PATENT DOCUMENTS

| 4,071,766 A * | 1/1978 | Kalman | ................... | H01J 37/20 |
| | | | | 250/440.11 |
| 2006/0249677 A1* | 11/2006 | Chao | ....................... | H01J 37/20 |
| | | | | 250/311 |

(Continued)

FOREIGN PATENT DOCUMENTS

| JP | 2006-313716 A | 11/2006 |
| JP | 2008-108429 A | 5/2008 |

(Continued)

OTHER PUBLICATIONS

International Search Report (PCT/ISA/210) issued in PCT Application No. PCT/JP2014/063148 dated Sep. 2, 2014 with English translation (six (6) pages).

(Continued)

*Primary Examiner* — Michael Maskell
(74) *Attorney, Agent, or Firm* — Crowell & Moring LLP (57) ABSTRACT

The objective of the present invention is to maintain the surrounding of a sample at atmospheric pressure and efficiently detect secondary electrons. In a sample chamber of a charged particle device, a sample holder (4) has: a gas introduction pipe and a gas evacuation pipe for controlling the vicinity of a sample (20) to be an atmospheric pressure environment; a charged particle passage hole (18) and a micro-orifice (18) enabling detection of secondary electrons (15) emitted from the sample (20), co-located above the sample (20); and a charged particle passage hole (19) with a hole diameter larger than the micro-orifice (18) above the sample (20) so as to be capable of actively evacuating gas during gas introduction.

8 Claims, 10 Drawing Sheets

(51) Int. Cl.
*H01J 37/18* (2006.01)
*H01J 37/285* (2006.01)
*G01N 23/22* (2006.01)
*H01M 8/04664* (2016.01)

(52) U.S. Cl.
CPC ... *H01J 2237/006* (2013.01); *H01J 2237/188* (2013.01); *H01J 2237/2003* (2013.01); *H01J 2237/2802* (2013.01); *H01J 2237/2806* (2013.01); *H01M 8/04671* (2013.01)

(58) Field of Classification Search
USPC .................................. 250/306, 307, 310, 311
See application file for complete search history.

(56) References Cited

U.S. PATENT DOCUMENTS

| | | | | |
|---|---|---|---|---|
| 2007/0029481 | A1* | 2/2007 | Morrison | H01J 37/20 250/311 |
| 2008/0093565 | A1 | 4/2008 | Yaguchi et al. | |
| 2009/0242763 | A1* | 10/2009 | Buijsse | H01J 37/023 250/307 |
| 2011/0303845 | A1* | 12/2011 | Yaguchi | H01J 37/20 250/310 |
| 2012/0104272 | A1* | 5/2012 | Cho | H01J 37/06 250/396 R |
| 2012/0305769 | A1 | 12/2012 | Yaguchi et al. | |
| 2014/0014835 | A1* | 1/2014 | Hosoya | H01J 37/20 250/307 |

FOREIGN PATENT DOCUMENTS

| | | |
|---|---|---|
| JP | 2011-14244 A | 1/2011 |
| JP | 2011-175809 A | 9/2011 |
| JP | 2013-20747 A | 1/2013 |
| WO | WO 2012/120726 A1 | 9/2012 |

OTHER PUBLICATIONS

Japanese language Writing Opinion (PCT/ISA/237 Form) issued in PCT Application No. PCT/JP2014/063148 dated Sep. 2, 2014 (five (5) pages).

* cited by examiner

SEM and STEM images of Pt/C during air injection

400°C, 5.4×10$^{-1}$ Pa(objective) in air at 300kV
10 min after gas injection

SAMPLE HOLDER AND CHARGED PARTICLE DEVICE

TECHNICAL FIELD

The present invention relates to an environmental control charged particle observation system. The system is used, in observation of a sample with a charged particle device e.g. an electron microscope, for efficiently detecting secondary electrons generated from the sample and performing efficient heating-observation on the sample while controlling the pressure in the vicinity of the sample. Accordingly, in analysis of degradation process in a recent fuel cell or the like, it is greatly useful for observation of dynamic change of the structure upon gas introduction and heating, by coordinating the observation environment of the electron microscope with actual operational environment.

BACKGROUND ART

In a charged particle device e.g. an electron microscope, in observation of a sample using a transmission electron image or a secondary electron image, in the field of electron microscope, observation is basically performed in a state where high-vacuum environment is maintained in the vicinity of the sample, in accordance with kind of charged particles to be detected for observation. However, in recent years, it is necessary to observe the sample in an actual operational environment. For example, when the dynamic change of the sample is observed while the sample is heated, a technique of performing observation in a state where the surrounding of the sample is in a low-vacuum state while introducing gas is being established. At this time, it is necessary that the charged particle device does not adversely affect the electron gun. There is a large limit on maintenance of the pressure in the vicinity of the sample at the actual operational environment, i.e. so-called atmospheric pressure. It is necessary to provide a holder for loading the sample with a structure for this purpose.

For example, in observation of the sample, a structure to isolate only the surrounding of the sample, using a thin film which charged particles pass through such as a diaphragm, above and below the sample, to attain atmospheric pressure in the vicinity of the sample, is known (Japanese Unexamined Patent Application Publication No. 2011-175809).

Further, there is a sample heating holder with a gas introduction mechanism, for observing the dynamic change of the sample when heated while controlling the pressure by blowing arbitrarily selected gas to the sample while heating the sample (Japanese Unexamined Patent Application Publication No. 2008-108429).

CITATION LIST

Patent Literature

Patent literature 1: Japanese Unexamined Patent Application Publication No. 2011-175809
Patent literature 2: Japanese Unexamined Patent Application Publication No. 2008-108429

SUMMARY OF INVENTION

Technical Problem

The above-described techniques are particularly concerned with observation using a transmission electron image. There has not been any technique of simultaneous observation of the transmission electron image and secondary electron image. Since only the surrounding of the sample is maintained at atmospheric pressure, the secondary electrons are blocked with the diaphragms and the secondary electrons cannot be detected.

Accordingly, to detect secondary electrons and perform observation using them, a holder, provided with a secondary electron detection passage above a sample using a minute orifice, and a coil heater for heating the sample via the orifice on a charged particle passage, is to be contrived and proposed. It is possible to observe dynamic change of the sample with detection of secondary electrons by controlling the pressure in the vicinity of the sample and heating the sample by introduction of gas.

That is, the present invention has an object to maintain the surrounding of a sample at atmospheric pressure and efficiently detect secondary electrons.

Solution to Problem

To attain the above object, the present invention adopts the configuration in the claims.

For example, one of the features is to enable pressure control in the vicinity of the sample and to efficiently detect secondary electrons, to observe dynamic change of the sample. Further, in control of the pressure in the vicinity of the sample, it is a sample holder having a differential exhaust hole to avoid advertise effect on the electron gun of the charged particle device e.g. electron microscope. The holder has a minute orifice as a secondary electron passage. It is provided with a gas introduction nozzle and a minute vacuum gauge for control of the pressure in the vicinity of the sample. Further, it has a heater for heating the sample.

Further, to maintain the surrounding of the sample in the atmospheric pressure environment, it is necessary to isolate only the surrounding of the sample from a sample chamber of the charged particle device and perform gas introduction. At this time, a diaphragm is used in the charged particle passage for observation of the sample. Although the charged particles pass through the diaphragm, detection of the secondary electrons is impossible, which adversely affects the observation. Regarding this problem, in the present invention, for example, when the sample holder is used, a minute orifice is provided above the sample, while a diaphragm is provided below the sample, with respect to the charged particle passage. With this configuration, the surrounding of the sample is maintained in the atmospheric pressure environment. Further, observation using secondary electrons is possible, thus the problem is solved.

Note that when the sample holder is used, since the minute orifice for the secondary electron passage is also used as an exhaust hole upon gas introduction, when it is overlapped with a passage hole for charged particles generated from the electron gun of the charged particle device e.g. an electron microscope, adverse effect such as degradation of the electron gun might occur. On the other hand, in the present invention, for example, by shifting the position of the charged particle passage hole from the minute orifice provided in the sample holder, the gas exhausted from the minute orifice is not directly exhausted to the electron gun, thus the problem is solved. Otherwise, when a larger exhaust hole is provided on the opposite side to the minute orifice of the sample holder, the gas is exhausted from the larger exhaust hole. Even this configuration, where the charged particle passage hole and the minute orifice are provided coaxially, does not adversely affect the electron gun. Thus the problem is solved.

Advantageous Effects of Invention

With the present invention, it is possible to observe dynamic change using secondary electrons while controlling the pressure in the vicinity of a desired sample. Further, since it is possible to perform observation while heating the sample, the invention greatly contributes to research of degradation process in the field of fuel cell. Further, it is possible to load, in addition to a powder sample, a micro sample formed with the charged particle device e.g. a focused ion beam processing observation device, in the sample holder according to the present invention. Accordingly, it is possible to greatly reduce working time from process to observation by enabling all the series of work steps from process to observation with one holder, which contributes to rapid advancement of researches in various fields.

BRIEF DESCRIPTION OF DRAWINGS

FIGS. 10A and 10B show cross-sectional diagrams of the tip of the sample holder according to an embodiment of the present invention.

FIGS. 12a-12C are explanatory diagrams schematizing a series of operations from manufacture to observation of the sample at the tip of the sample holder according to an embodiment of the present invention.

DESCRIPTION OF EMBODIMENTS

Figure 1:
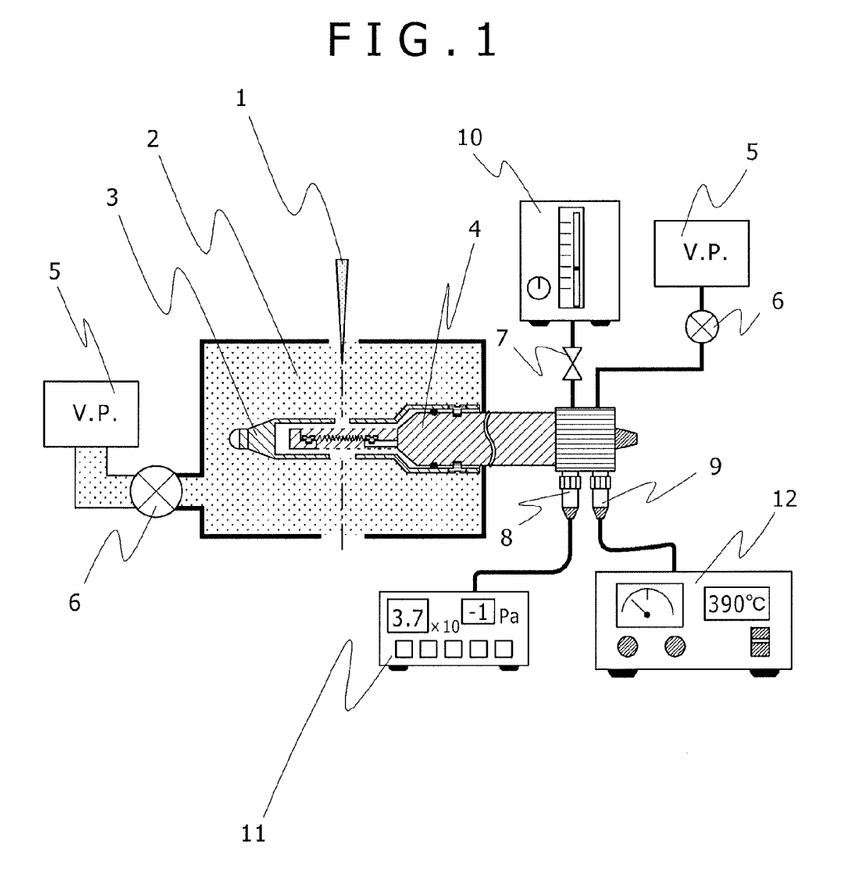
FIG. 1 is a schematic diagram of a charged particle device sample chamber and a sample holder according to an embodiment of the present invention, showing the positional relationship among charged particles in a charged particle device sample chamber for observation, a charged particle passage provided in the sample holder, and a sample.

FIG. 1 shows a basic conceptual diagram of the present invention. With respect to a sample holder tip cap 3 to block only the sample holder 4 provided in a charged particle device sample chamber 2 and the surrounding of the sample 20, the sample holder tip cap 3 is provided with a charged particle passage hole (micro orifice) 18 through which charged particles A1 pass, to enable observation of charged particles. The charged particle device sample chamber 2 is maintained in a high vacuum state with a vacuum pump 5 and a valve 6. The sample holder 4 has a gas introduction pipe 26 and a gas exhaust pipe 25 to vary the pressure in the vicinity of the sample 20. It has a structure to supply gas from a gas storage unit 10 via the gas pressure control valve 6 to control a flow rate upon gas introduction, and to exhaust the gas with the exhaust vacuum pump 5 and the valve 6. Further, a pressure gauge 11 to detect the pressure in the vicinity of the sample 20 is connected to the sample holder 4. Further, the sample holder 4 is provided with a heater 16 to heat the sample 20. A sample-heating temperature control unit 12 to control the temperature of the heater 16 is connected to the sample holder.

Figure 2:
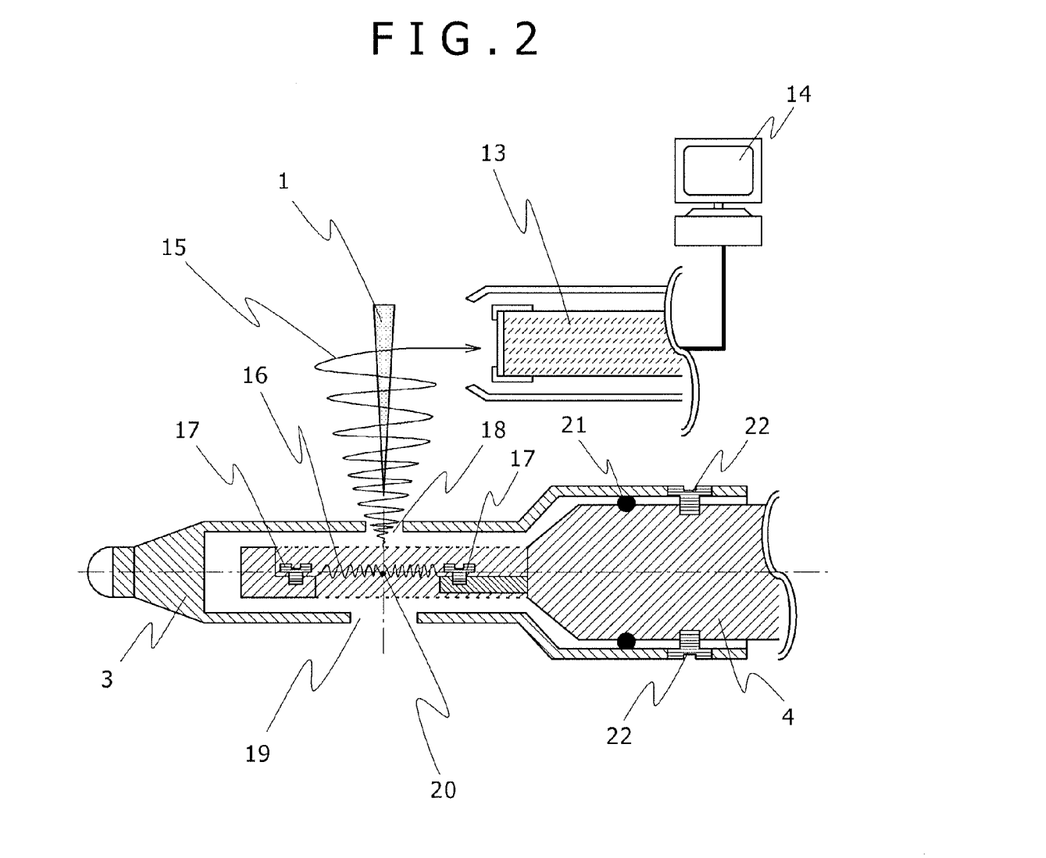
FIG. 2 shows the positional relationship between secondary electrons, emanated from the tip of the sample holder and from the sample, and a secondary electron detector, according to an embodiment of the present invention.

FIG. 2 shows a conceptual diagram of a detailed structure of the tip of the sample holder 4 described in FIG. 1. The sample holder 4 is provided with an O-ring 21 to atmospherically block only the surrounding of the sample 20 with the sample holder tip cap 3. Further, it has a sample holder tip cap fixing screw 22 to fix the sample holder tip cap 3. In the sample holder tip cap 3, the charged particle passage hole (micro orifice) 18 through which the charged particles A1 pass is provided in positions above and below the sample 20. The charged particle passage hole (micro orifice) 18 above the sample 20 has a hole diameter to pass secondary electrons 15 emanated from the sample 20. It is possible to perform image observation with an image display unit 14 via secondary electron detector 13.

Figure 13:
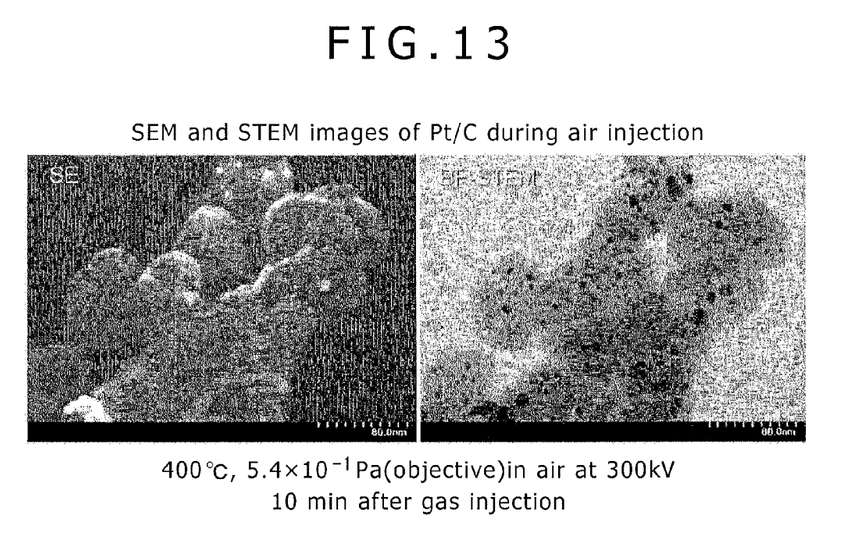
FIG. 13 shows an embodiment of sample observation according to the present invention.

FIG. 13 shows an observation example at this time. In FIG. 13, an observation image with the secondary electrons 15 and an observation image with transmission electrons are contrasted with each other. It is possible to enable surface observation using the secondary electron image in addition to observation of inner structure of material using the transmission image upon in situ observation of structural change of the sample, as a new in situ observation technique. Further, the sample holder 4 is provided with the heater 16 in which the sample 20 is loaded, and has a screw to fix the heater 16. To enhance exhaust capacity, a charged particle passage and gas exhaust hole 19 below the sample 20 has a hole diameter larger than that of the charged particle passage hole (micro orifice) 18 above the sample 20. With this configuration, the gas exhausted upon gas introduction is exhausted in a direction lower than an occurrence direction of the charged particles A1. Accordingly, a structure not to influence the electron gun of the charged particle source 28 e.g. an electron microscope is obtained.

Figure 5:
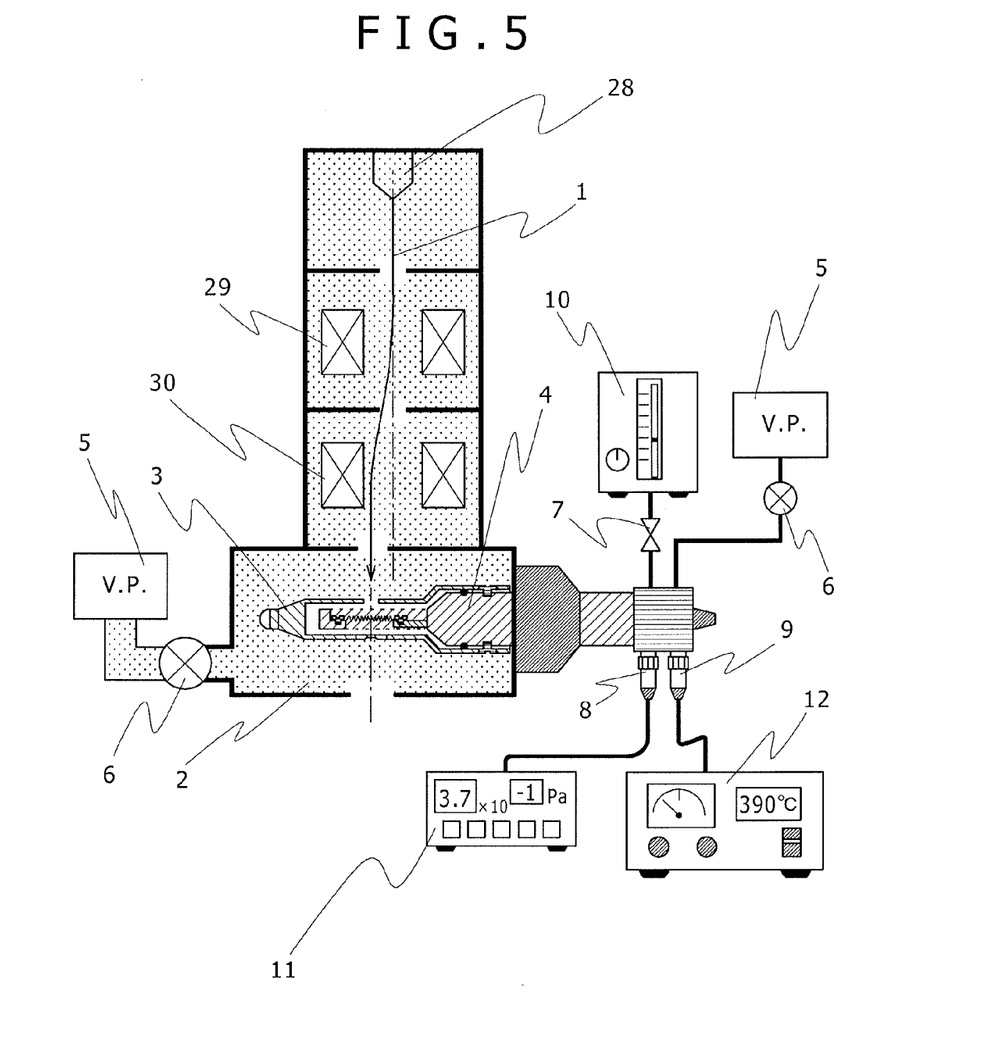
FIG. 5 is a schematic diagram of the charged particle device and the sample holder according to an embodiment of the present invention, showing the positional relationship among the charged particles in the charged particle device sample chamber for observation, the charged particle passage provided in the sample holder, and the sample.

FIG. 5 shows a basic conceptual diagram of the present invention. With respect to the sample holder tip cap 3 to block only the sample holder 4 provided in the charged particle device sample chamber 2 and the surrounding of the sample 20, the sample holder tip cap 3 is provided with the charged particle passage hole (micro orifice) 18 through which the charged particles A1 pass, to enable observation of charged particles. At this time, in the sample holder tip cap 3, the charged particle passage hole (micro orifice) 18 through which the charged particles A1 pass is provided above the sample 20, and below the sample 20, a diaphragm 32 separates the surrounding of the sample 20 from the charged particle device sample chamber 2 for passing the charged particles A1. Further, the charged particle passage hole (micro orifice) 18 provided above the sample 20 at the sample holder tip cap 3 is provided in a position not coaxial with a charged particle passage and gas exhaust hole 31 for charged particles emanated from the charged particle source 28. Accordingly, the gas exhausted from the charged particle passage hole (micro orifice) 18 positioned above the sample 20 at the sample holder tip cap 3 is injected in a direction different from the occurrence direction of the charged particles A1. Thus a structure not to influence the electron gun of the charged particle source 28 e.g. an electron microscope is obtained. Further, constituent elements of the charged particle device sample chamber 2 and the sample holder 4 are the same as those in FIG. 1.

First Embodiment

Figure 3:
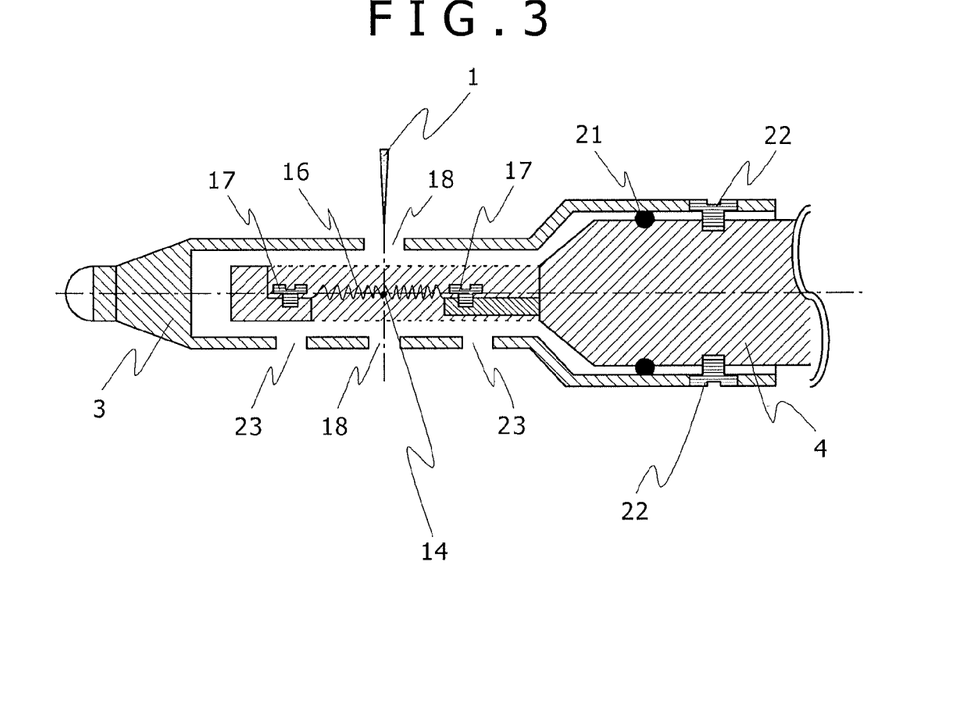
FIG. 3 shows a cross-sectional diagram of the tip of the sample holder according to an embodiment of the present invention.

FIG. 3 shows an embodiment of the present invention, and shows the tip of the sample holder 4 described in FIG. 1 in detail. As in the case of FIG. 2, the sample holder 4 is provided with the O-ring 21 to atmospherically block only the surrounding of the sample 20 with the sample holder tip cap 3. Further, it has the sample holder tip cap fixing screw 22 to fix the sample holder tip cap 3. In the sample holder tip cap 3, the charged particle passage hole (micro orifice) 18 through which the charged particles A1 pass is provided in the positions above and below the sample 20. The charged particle passage hole (micro orifice) 18 above the sample 20 has a hole diameter to pass the secondary electrons 15 emanated from the sample 20. It is possible to enable image observation with the image display unit 14 via the secondary electron detector 13. Further, in addition to the charged particle passage and gas exhaust hole 19 below the sample 20, a structure to positively perform differential exhaust in a direction different from the direction of generation source of the charge particles A1 by providing a gas exhaust hole 23 is provided. With this configuration, the gas exhausted upon gas introduction is exhausted in a direction lower than the occurrence direction of the charged particles A1, which does not influence the electron gun of the charged particle source 28 e.g. an electron microscope.

Second Embodiment

Figure 4:
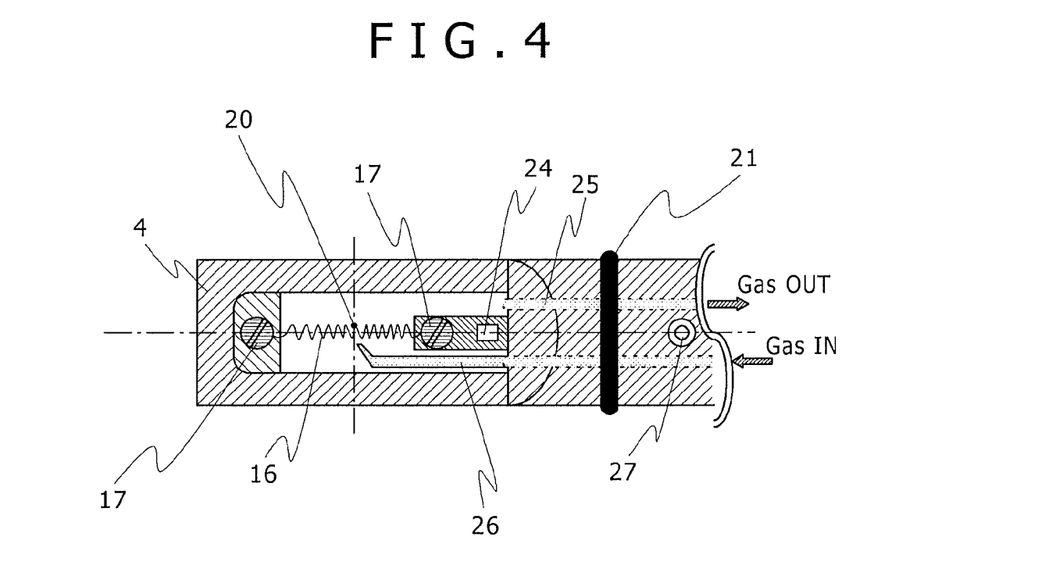
FIG. 4 shows a bird's-eye view of the tip of the sample holder according to an embodiment of the present invention.

FIG. 4 shows an embodiment of the present invention and is a detailed diagram of the tip of the sample holder 4. The sample holder 4 is provided with the heater 16 for loading the sample 20, and the sample 20 is loaded there. Further, it has a structure provided with the gas introduction pipe 26 and the gas exhaust pipe 25 directed to the sample 20, and has a minute pressure measuring element 24 to detect the pressure in the vicinity of the sample 20.

Third Embodiment

Figure 6:
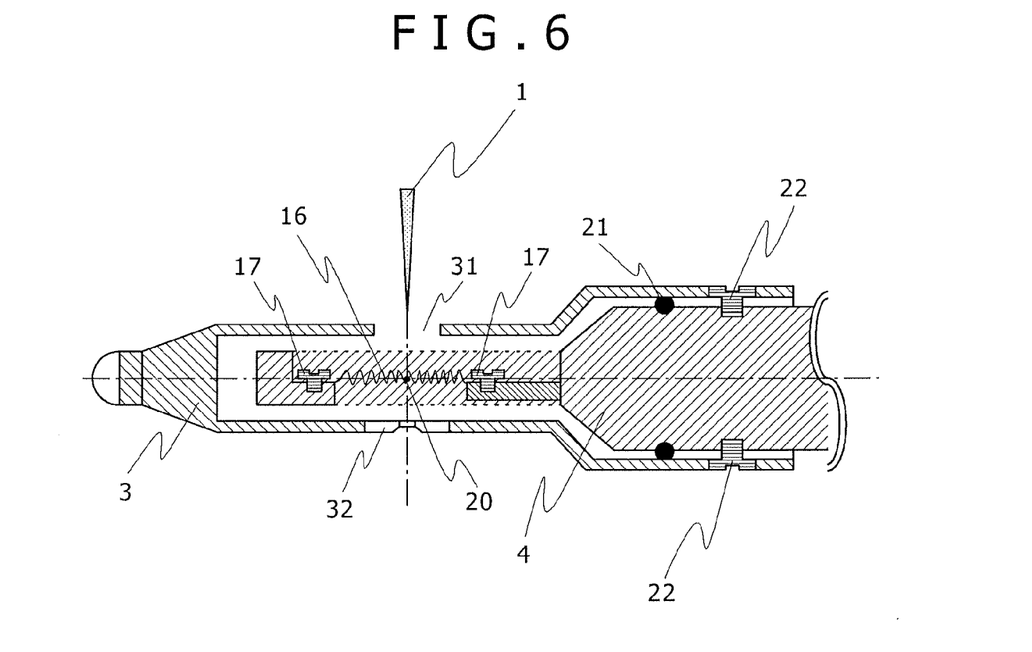
FIG. 6 shows a cross-sectional diagram of the tip of the sample holder according to an embodiment of the present invention.
Figure 7:
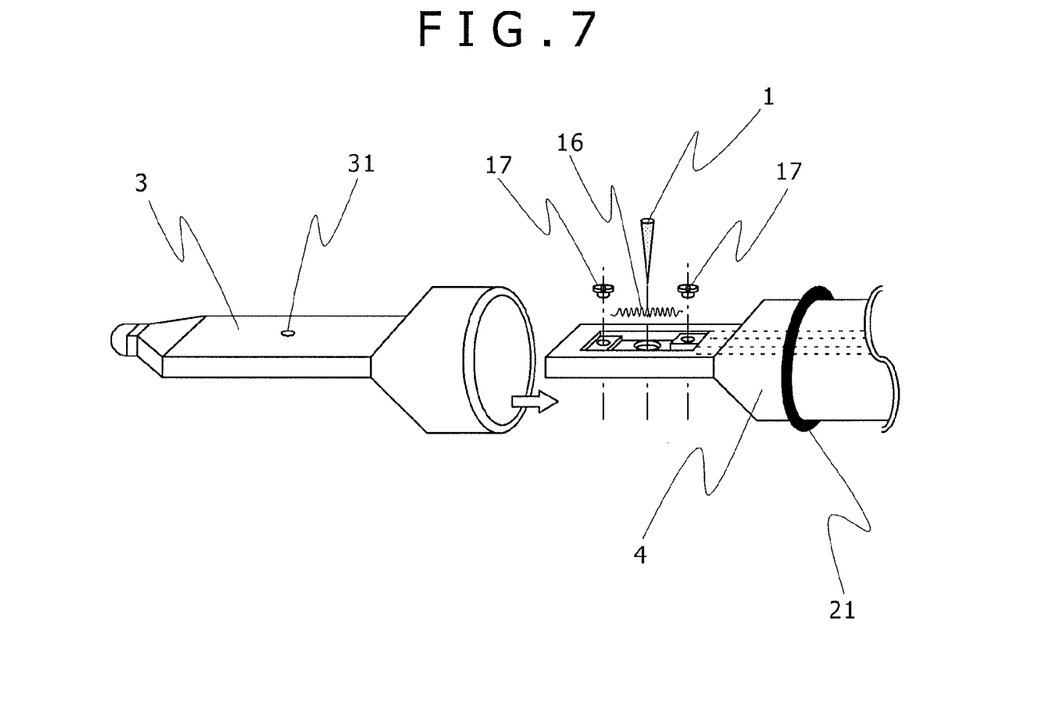
FIG. 7 shows a development view of the tip of the sample holder according to an embodiment of the present invention.
Figure 8:
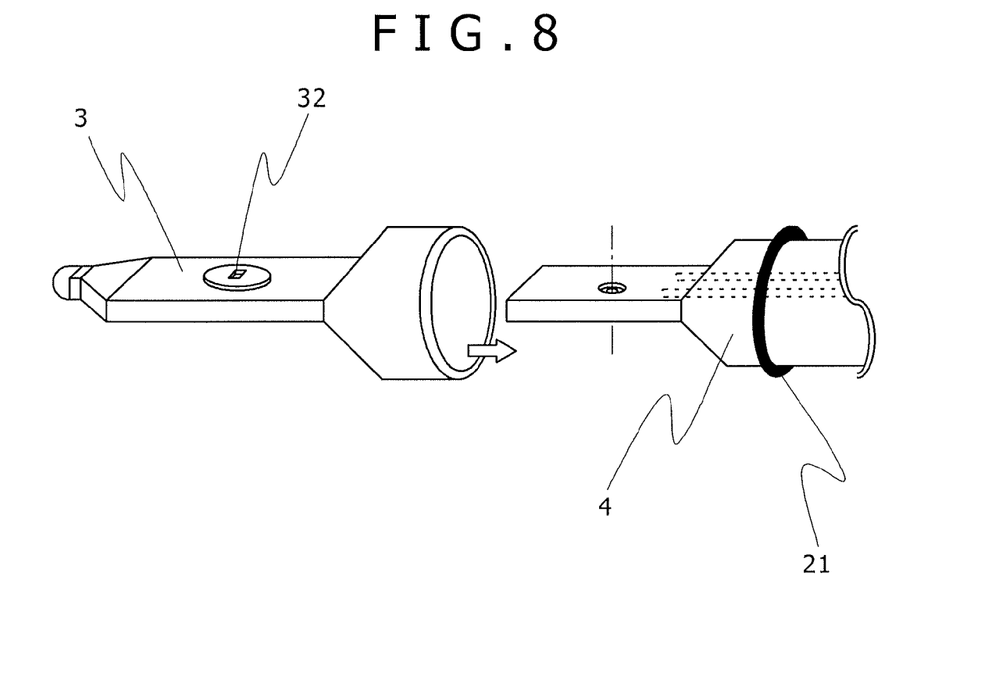
FIG. 8 shows a development view of the tip of the sample holder according to an embodiment of the present invention.
Figure 9:
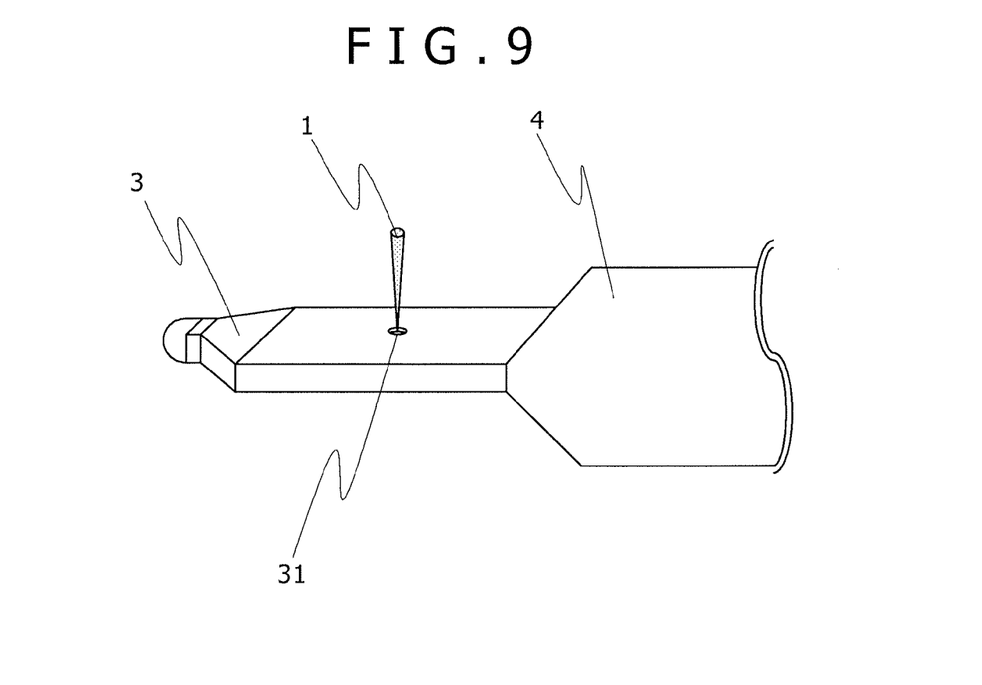
FIG. 9 shows the positional relationship between the tip of the sample holder and the charged particles, according to an embodiment of the present invention.

FIG. 6 shows an embodiment of the present invention and shows the tip of the sample holder 4 described in FIG. 5 in detail.

Fourth Embodiment

Figure 10A:
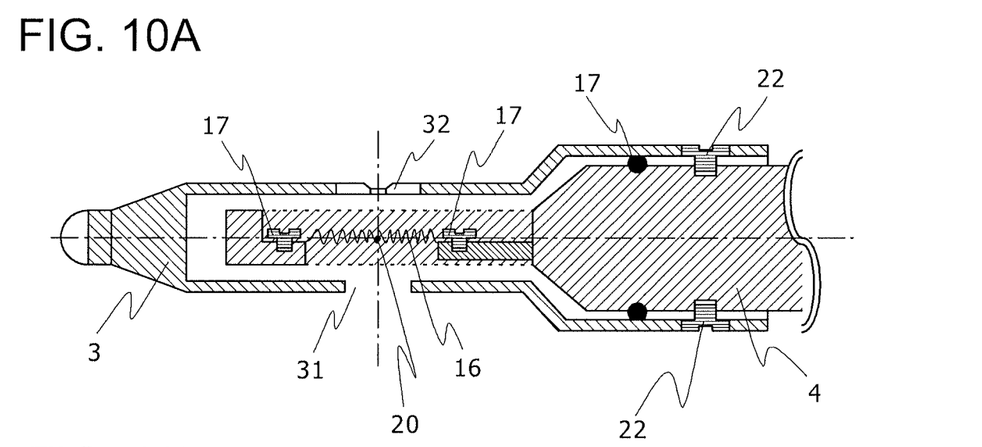
FIG. 10A is a diagram where a diaphragm is provided above the sample at the tip of the sample holder.
Figure 10B:
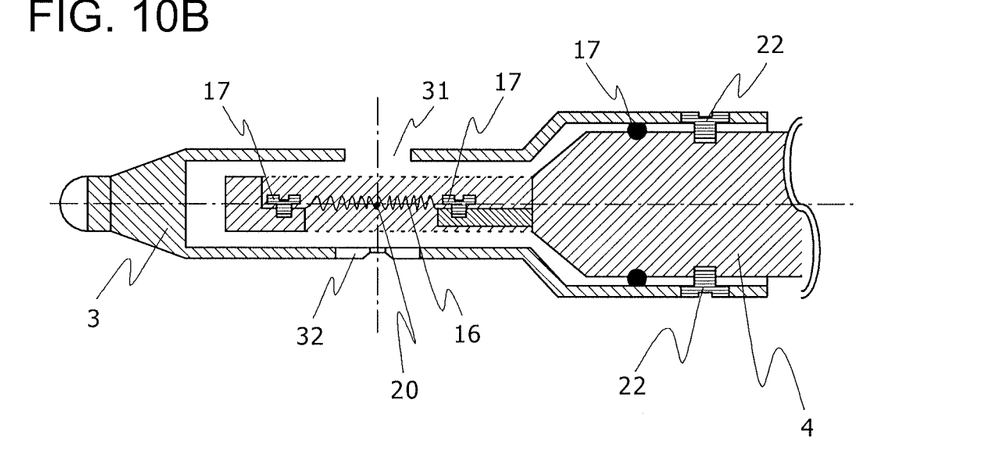
FIG. 10B is a diagram where the diaphragm is provided below the sample at the tip of the sample holder.

FIG. 10 shows an embodiment of the present invention, and shows an example where the positions of the diaphragm 32 and the charged particle passage and gas exhaust hole 19 corresponding to the charged particles A1 passages above and below the sample 20 at the tip of the sample holder 4 described in FIG. 6 are reversed in accordance with purpose. For example, in the case of observation using transmission electrons, to avoid trouble of the charged particle source 28 due to exhaust from the charged particle passage and gas exhaust hole 19, the sample holder tip cap 3 is provided as shown in FIG. 10-(a). In the case of observation using the secondary electrons 15, the sample holder tip cap 3 is provided, with the arrangement relationship in FIG. 5 as a condition, as shown in FIG. 10-(b).

Fifth Embodiment

Figure 11:
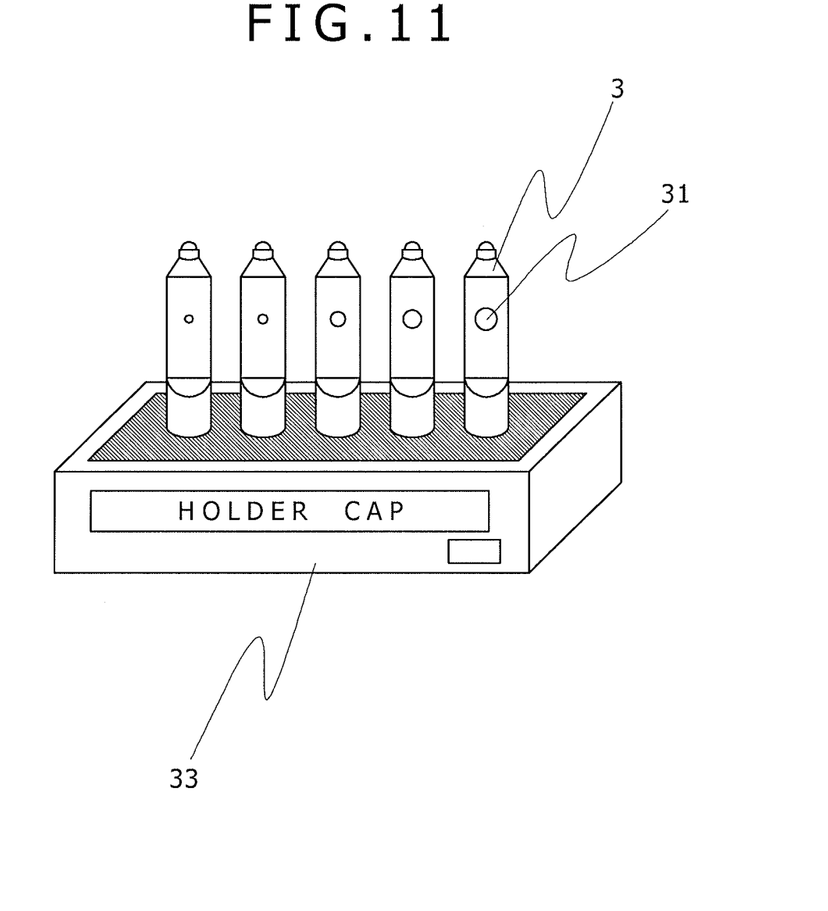
FIG. 11 is a schematic diagram of a cap at the tip of the sample holder according to an embodiment of the present invention.

FIG. 11 shows an embodiment of the present invention. It has a structure changeable by a user in accordance with a pressure condition in the vicinity of the sample 20, by preparing plural sample holder tip caps 3 to be attached to the tip of the sample holder 4 having different hole diameters of the charged particle passage and gas exhaust hole 19.

Sixth Embodiment

Figures 12A, 12B, 12C:
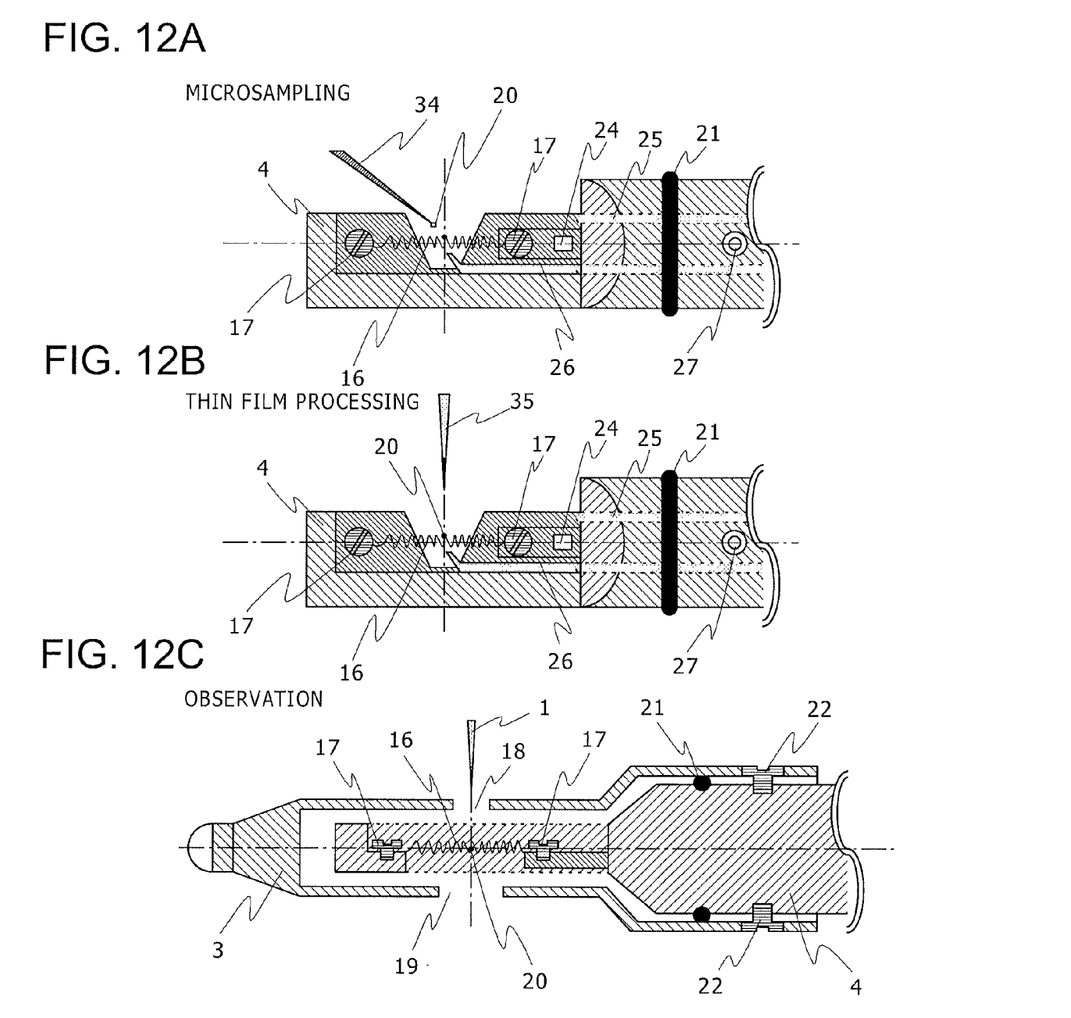
FIG. 12A is a bird's-eye view of the tip of the sample holder schematically showing sample loading by microsampling.
FIG. 12B is a bird's-eye view of the tip of the sample holder schematically showing thin film processing on the sample.
FIG. 12C is a cross-sectional diagram of the tip of the sample holder schematically showing observation.

FIG. 12 shows an embodiment of the present invention. The sample holder 4 has a structure provided with a notch in an emission direction of charged particles B35 e.g. focused ion beam for loading the micro sample 20 manufactured by microsampling with the charged particle device e.g. a focused ion beam process device. With this structure, it is possible to enable thin film processing on the sample 20 with the charged particles B35 e.g. a focused ion beam. Further, in the structure, the sample holder tip cap 3 is attached, and in addition, the direction of the sample 20 is rotated at 90°, for observation of the thin-film processed sample 20 with the charged particle device e.g. an electron microscope different from the aforementioned device.

REFERENCE SIGNS LIST 1 charged particles A
2 charged particle device sample chamber
3 sample holder tip cap
4 sample holder
5 vacuum pump
6 valve
7 gas pressure control valve
8 micro-pressure measurement element connector
9 sample heating connector
10 gas storage unit
11 pressure gauge
12 sample-heating temperature control unit
13 secondary electron detector
14 image display unit
15 secondary electrons
16 heater (sample loading portion)
17 heater fixing screw
18 charged particle passage hole (micro orifice)
19 charged particle passage and gas exhaust hole
20 sample
21 O-ring
22 sample holder tip cap fixing screw
23 gas exhaust hole
24 minute pressure measuring element
25 gas exhaust pipe
26 gas introduction pipe
27 sample holder tip cap fixing screw hole
28 charged particle source
29 condenser lens A
30 condenser lens B
31 charged particle passage and gas exhaust hole
32 diaphragm 33 sample holder tip cap storage box
34 microprobe
35 charged particles B

The invention claimed is:

1. A sample holder, comprising:
a gas introduction pipe;
a gas exhaust pipe, wherein the gas introduction pipe and the gas exhaust pipe are arranged to control surrounding of a sample in atmospheric pressure environment in a sample chamber of a charged particle device;
a micro orifice, disposed in an upper portion of the sample holder above the sample, that allows for detection of secondary electrons emanated from the sample; and
a charged particle passage hole, disposed in a lower portion of the sample holder below the sample, that has a larger diameter than a diameter of the micro orifice above the sample for positively performing exhaust upon gas introduction;
wherein a sample holder tip cap is selectable from a plurality of sample holder tip caps having different hole diameters of the micro orifice.

2. The sample holder according to claim 1, wherein a state of the sample in gas atmosphere upon sample heating is observable by having a heater for heating the sample.

3. The sample holder according to claim 1, having one or more gas exhaust holes in addition to the charged particle passage hole positioned below the sample.

4. The sample holder according to claim 1, having a minute pressure measuring element for checking the pressure in the vicinity of the sample.

5. A sample holder provided in a charged particle device, the sample holder comprising:
a micro orifice, disposed in an upper portion of the sample holder above a sample, and arranged to avoid coaxial positioning of an emission direction of charged particles emanated from a charged particle generation source with a sample center, in the charged particle device, the micro orifice allowing for detection of secondary electrons emanated from the sample;
a gas introduction pipe;
a gas exhaustion pipe, wherein the gas introduction pipe and the gas exhaust pipe are arranged to control surrounding of the sample in atmospheric pressure environment; and
a diaphragm, through which the charged particles are transmitted, disposed in a lower portion of the sample holder below the sample;
wherein a sample holder tip cap is selectable from a plurality of sample holder tip caps having different hole diameters of the micro orifice.

6. The sample holder according to claim 5, wherein the sample holder tip cap has a structure where a position of the diaphragm is changeable to a position above or below the sample.

7. The sample holder according to claim 1, having a structure capable of performing a series of operations including processing the sample and observing the sample with different charged particles, and arbitrarily changing a sample direction with respect to an emission direction of the charged particles.

8. A charged particle device comprising:
a sample holder having a sample holding part that holds the sample, and an environment control part, including the sample holding part, that controls environment in the vicinity of the sample, and has a hole in a predetermined size above the sample;
a charged particle generation source that generates charged particles;
a charged particle passage and gas exhaust hole that receives charged particles emanated from the charged particle generation source and exhausts the received charged articles from the charged particle device upon gas introduction;
a lens that adjusts an emission direction of the charged particles generated from the charged particle generation source;
a detector that detects secondary electrons generated from the sample; and
wherein the hole of the sample holder is provided in a position not coaxial with the charged particle passage and gas exhaust hole, and by adjusting the emission direction of the charged particles generated from the charged particle generation source with the lens, the charged particles generated from the charged particle generation source are emitted through the hole of the sample holder to the sample, while the secondary electrons generated from the sample are discharged from the sample holder through the hole of the sample holder, and detected with the detector;
wherein a sample holder tip cap is selectable from a plurality of sample holder tip caps having different hole diameters of the micro orifice.

* * * * *